(12) United States Patent
Shilev

(10) Patent No.: US 8,628,524 B2
(45) Date of Patent: Jan. 14, 2014

(54) RETURN ELECTRODE DETECTION AND MONITORING SYSTEM AND METHOD THEREOF

(75) Inventor: Nickolay D. Shilev, Sofia (BG)

(73) Assignee: Bovie Medical Corporation, Clearwater, FL (US)

( * ) Notice: Subject to any disclaimer, the term of this patent is extended or adjusted under 35 U.S.C. 154(b) by 885 days.

(21) Appl. No.: 12/761,520

(22) Filed: Apr. 16, 2010

(65) Prior Publication Data

US 2010/0331835 A1 Dec. 30, 2010

Related U.S. Application Data

(60) Provisional application No. 61/172,944, filed on Apr. 27, 2009.

(51) Int. Cl.
*A61B 18/10* (2006.01)

(52) U.S. Cl.
USPC .......................................................... 606/35

(58) Field of Classification Search
USPC .......................................... 606/27, 34, 35, 41
See application file for complete search history.

(56) References Cited

U.S. PATENT DOCUMENTS

| | | | |
|---|---|---|---|
| 4,200,104 A | 4/1980 | Harris | |
| 4,416,276 A | 11/1983 | Newton et al. | |
| 4,416,277 A * | 11/1983 | Newton et al. | 606/35 |
| 4,754,757 A | 7/1988 | Feucht | |
| 5,087,257 A | 2/1992 | Farin et al. | |
| 5,830,212 A | 11/1998 | Cartmell et al. | |
| 5,836,942 A | 11/1998 | Netherly et al. | |
| 5,849,009 A * | 12/1998 | Bernaz | 606/36 |
| 6,565,559 B2 | 5/2003 | Eggleston | |
| 6,582,424 B2 | 6/2003 | Fleenor et al. | |
| 6,860,881 B2 | 3/2005 | Sturm et al. | |
| 2007/0049916 A1 | 3/2007 | Isaacson et al. | |
| 2009/0198230 A1 * | 8/2009 | Behnke et al. | 606/35 |

* cited by examiner

*Primary Examiner* — Michael Peffley
*Assistant Examiner* — Daniel Fowler
(74) *Attorney, Agent, or Firm* — Gerald E. Hespos; Michael J. Porco; Matthew T Hespos

(57) ABSTRACT

A return electrode detection and monitoring system and method thereof are provided. The system and method of the present disclosure provide for a combined universal recognition feature, that is to identify whether a return or neutral electrode coupled to an electrosurgical generator is a capacitive electrode or a split or non-split (solid) resistive electrode. Furthermore, the system and method will monitor both capacitive and resistive return electrodes when the electrosurgical generator is operating in the 4 Mhz range to notify an operator when the return electrode is not coupled enough which would effect power delivery to the patient and hence effect on the targeted tissue.

21 Claims, 4 Drawing Sheets

RETURN ELECTRODE DETECTION AND MONITORING SYSTEM AND METHOD THEREOF

PRIORITY

This application claims priority to U.S. Provisional Patent Application No. 61/172,944 filed on Apr. 27, 2009, the contents of which are hereby incorporated by reference in its entirety.

BACKGROUND

1. Field

The present disclosure relates generally to electrosurgery and electrosurgical systems and apparatuses, and more particularly, to a return electrode detection and monitoring system and method thereof.

2. Description of the Related Art

Electrosurgery is a term used to describe the passage of high-frequency (i.e., radio frequency) electrical current through tissue to create a desired clinical tissue effect. Through this technique, the target tissue, acting as a resistor in an electrical circuit, is heated by its conduction of the electrical current. Electrocautery, as distinguished from electrosurgery, uses an electrical current to heat a surgical instrument, which in turn conveys that heat to the target tissue. Electrosurgical electrode tips remain cool while targeted tissues heat up, primarily because the electrodes have much lower impedance than the adjacent targeted tissues. Electrosurgical tissue effects include cutting, coagulation, desiccation and fulguration. In addition, modern electrosurgical generators can create blended modes of operation under which a surgeon can for example, cut and coagulate simultaneously.

In electrosurgery, there are two types of electrodes: mono-polar and bipolar. Mono-polar electrodes pass RF electrical current from an electrosurgical generator through an active electrode into targeted tissue, through the patient, a dispersive electrode (e.g., a return electrode or pad), and back into the electrosurgical generator. If the return electrode is properly placed relative to the patient and surgical site, the electrosurgical tissue effects occur only at the active electrode and not the dispersive electrode. On the other hand, bipolar electrodes are arranged in pairs (or poles, "+/−" and "−/+") and form part of the surgical instrument (e.g., electrosurgical forceps) without the need for a separate return electrode (grounding) plate attached to the patient. The intended flow of current is between the pair of bipolar electrodes (from "+/−" to "−/+"), which are usually close together and use relatively low voltage.

In monopolar electrosurgery, the patient return electrode is placed at a remote site from the active or source electrode and is typically in the form of a pad adhesively adhered to the patient. The return electrode has a large patient contact surface area to minimize heating at that site since the smaller the surface area, the greater the current density and the greater the intensity of the heat. That is, the area of the return electrode that is adhered to the patient is important because it is the current density of the electrical signal that heats the tissue. A larger surface contact area is desirable to reduce heat intensity. Return electrodes are sized based on assumptions of the maximum current seen in surgery and the duty cycle (the percentage of time the generator is on) during the procedure.

The first types of return electrodes were in the form of large metal plates covered with conductive jelly. Later, adhesive electrodes were developed with a single metal foil covered with conductive jelly or conductive adhesive. However, one problem with these adhesive electrodes was that if a portion peeled from the patient, the contact area of the electrode with the patient decreased, thereby increasing the current density at the adhered portion and in turn increasing the heat applied to the tissue. This risked burning the patients in the area under the adhered portion of the return electrode if the tissue was heated beyond the point where the circulation could cool the skin.

To address this problem, split return electrodes and hardware circuits, generically called Return Electrode Contact Quality Monitors (RECQMs), were developed. Typically, these split electrodes consist of two separate conductive foils or plates connected by a resistive element and are usually referred to as resistive type return electrodes. The hardware circuit uses an AC signal between the two electrode halves to measure the impedance therebetween. This impedance measurement is indicative of how well the return electrode is adhered to the patient since the impedance between the two halves is directly related to the area of patient contact. That is, if the electrode begins to peel from the patient, the impedance increases since the contact area of the electrode decreases. Current RECQMs are designed to sense this change in the contact impedance (between the two plates) so that when the percentage increase in impedance exceeds a predetermined value or the measured impedance exceeds a threshold level, the electrosurgical generator is shut down to reduce the chances of burning the patient. However, in situations where the impedance is within predetermined limits but full contact between the body of the patient and return electrode is not achieved, the power output of the electrosurgical generator is substantially the same when using a resistive type return electrode. In the resistive split or non-split electrode, the electrode is always touching the patient, so the power delivery is not affected however the contact impedance between the two plates or electrodes affects the current density. Increased current densities could lead to patient burns on the applied sites.

In the case of a capacitive return electrode, which is used in the 4 MHz range of a electrosurgical generator's working frequencies, the capacitance of the contact between the body and the return electrode could affect significantly the power output of the electrosurgical generator. In other words, being in series with the body resistance, the contact capacitance will increase or decrease the overall load impedance, changing the voltage drop across the body impedance, thus changing the power delivery, hence the tissue effect.

Therefore, a need exists for techniques for determining contact quality in an electrosurgical unit while using a capacitive type return electrode. Furthermore, a need exists for a apparatus for supplying electrosurgical energy that is compatible with both resistive and capacitive type return electrodes.

SUMMARY

A return electrode detection and monitoring system and method thereof are provided. The system and method of the present disclosure provide for a combined universal recognition feature, that is to identify whether a return or neutral electrode coupled to an electrosurgical generator is a capacitive electrode or a split or non-split (solid) resistive electrode. Furthermore, the system and method will monitor both capacitive and resistive return electrodes when the electrosurgical generator is operating in the 4 Mhz range to notify an operator when the return electrode is not coupled enough which would effect power delivery to the patient and hence effect on the targeted tissue.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
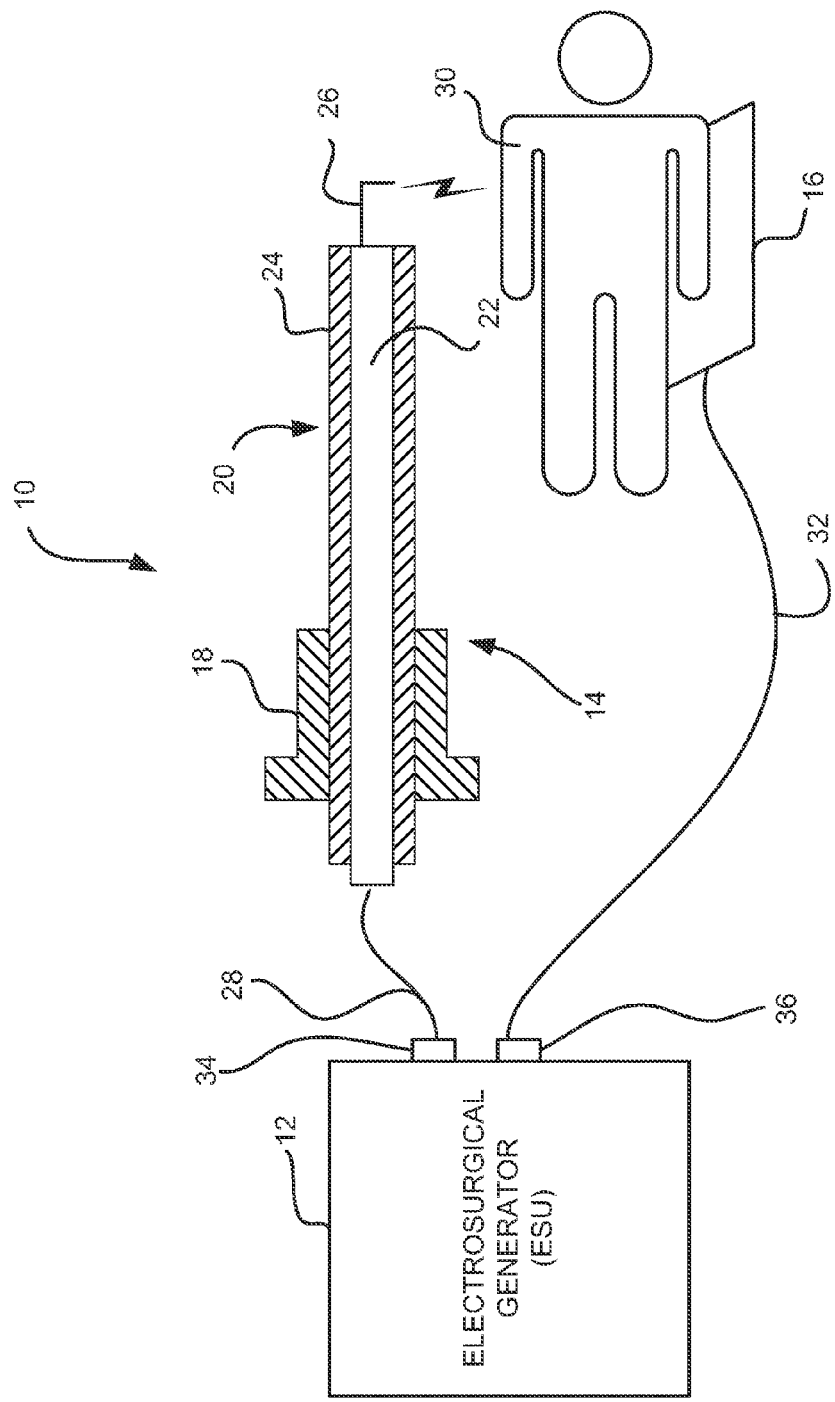
FIG. 1 is a schematic illustration of a monopolar electrosurgical system in accordance with an embodiment of the present disclosure.

Preferred embodiments of the present disclosure will be described hereinbelow with reference to the accompanying drawings. In the following description, well-known functions or constructions are not described in detail to avoid obscuring the present disclosure in unnecessary detail. In the drawings and in the description which follow, the term "proximal", as is traditional, will refer to the end of the device, e.g., instrument, handpiece, forceps, etc., which is closer to the user, while the term "distal" will refer to the end which is further from the user. Herein, the phrase "coupled" is defined to mean directly connected to or indirectly connected with through one or more intermediate components. Such intermediate components may include both hardware and software based components.

It should be understood that the elements shown in the figures may be implemented in various forms of hardware, software or combinations thereof. Preferably, these elements are implemented in a combination of hardware and software on one or more appropriately programmed general-purpose devices, which may include a processor, memory and input/output interfaces.

The present description illustrates the principles of the present disclosure. It will thus be appreciated that those skilled in the art will be able to devise various arrangements that, although not explicitly described or shown herein, embody the principles of the disclosure and are included within its spirit and scope.

All examples and conditional language recited herein are intended for pedagogical purposes to aid the reader in understanding the principles of the disclosure and the concepts contributed by the inventor to furthering the art, and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

Thus, for example, it will be appreciated by those skilled in the art that the block diagrams presented herein represent conceptual views of illustrative circuitry embodying the principles of the disclosure. Similarly, it will be appreciated that any flow charts, flow diagrams, state transition diagrams, pseudo-code, and the like represent various processes which may be substantially represented in computer readable media and so executed by a computer or processor, whether or not such computer or processor is explicitly shown.

A return electrode detection and monitoring system and method thereof are provided. The system and method of the present disclosure provide for a combined universal recognition feature, that is to identify whether a return or neutral electrode coupled to an electrosurgical generator is a capacitive electrode or a split or non-split (i.e., solid) resistive electrode.

Referring to FIG. 1, an electrosurgical system 10 is shown including an electrosurgical generator (ESU) 12, a laparoscopic instrument 14 and a return electrode 16. The electrosurgical generator 12 is configured for supplying electrosurgical energy via the laparoscopic instrument 14 to an operative site of a patient 30, e.g., tissue. The electrosurgical laparoscopic apparatus 14 includes a trocar sheath or cannula 18 which is conventionally used to provide a conduit through a patient's skin into the peritoneal cavity. Removably insertable through the trocar sheath is an active electrode probe or handpiece 20 which includes an active electrode 22 disposed within a passage of the handpiece and an insulative coating 24 thereon. The distal end of the electrode 20 includes a tip 26 for affecting a surgical procedure at the operative site. The tip 26 of the probe may be of different conventional shapes such as needle-shape, hook-shape, spatula-shape, graspers, scissors, etc. and serve various conventional functions such as suction, coagulation, irrigation, pressurized gas, cutting, etc. The instrument 14 is coupled to the generator 12 at an active output 34 via a power cord cable 28. The return electrode 16 is placed in contact with the patient 30 to return energy to the electrosurgical generator (ESU) 12 at a return input 36 via cable 32.

It is to be appreciated that although a laparoscopic instrument is shown and described other monopolar type electrosurgical instruments, e.g., an electrosurgical pencil, may be employed in accordance with the teachings of the present disclosure.

The electrosurgical generator 12 of the present disclosure operates with a working frequency of 4 MHz. One of the advantages of the 4 MHz working frequency is the ability to use a capacitive coupled return electrode (RE). This is widely used in veterinary operations, and is considered to be also a very convenient feature in plastic surgery. However, all the conventional ESU's, working at that frequency, employ with solid return electrodes. This provides a level of simplicity to the ESU system, but a different coupling capacitance of the return electrode will lead to different power output to the tissue with one and the same power setting. The system of the present disclosure measures the instantaneous capacitance of the return electrode (RE), and in the case it is not in some pre-defined limits or with a very low value, will alarm the operator and stop the RF power, until the proper capacitance with the body is restored. In addition, the system of the present disclosure is capable of recognizing and working with a resistive split electrode, which will give the operator an additional safety feature.

Figure 2:
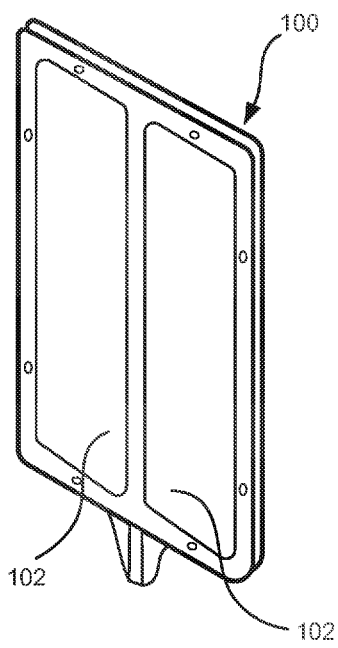
FIG. 2 is a perspective view of a capacitively coupled split electrode in accordance with an embodiment of the present disclosure.
Figure 3:
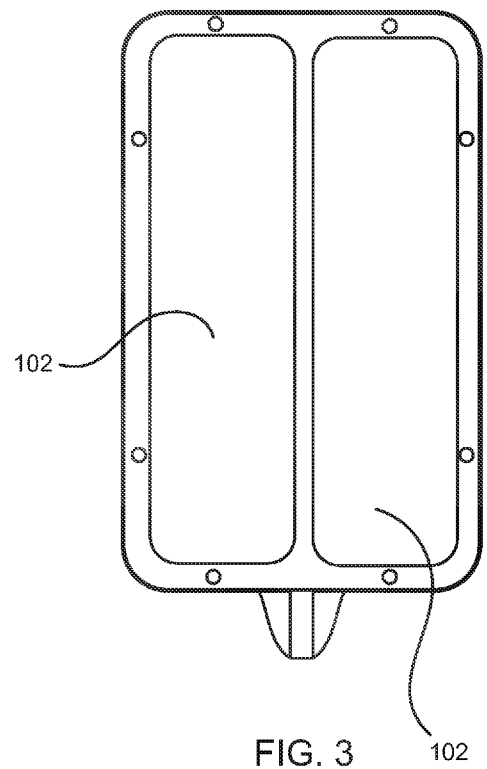
FIG. 3 is a top view of the capacitively coupled split electrode shown in FIG. 2.
Figure 4:
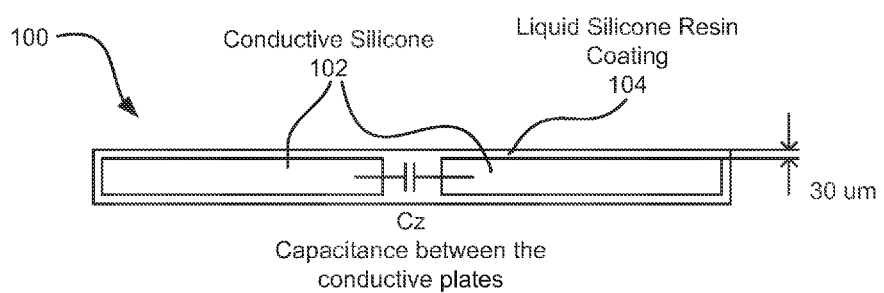
FIG. 4 is a cross sectional view of a capacitively coupled split electrode in accordance with an embodiment of the present disclosure.

The ESU of the present disclosure that operates at 4 MHz employs a return electrode 100 implemented using a reusable silicone split electrode 102, which surface is isolated with a thin (20-30 um) liquid silicone resin (LSR) layer 104, as shown in FIGS. 2-4. The return electrode 100 includes two electrode portions 102 constructed of a conductive silicone. Inside each electrode portion 102 is a grid of a buss wire, which gives additional strength and improves the conductivity and equipotential status of the return electrode. The LSR layer 104 acts as the dielectric forming the capacitance between the conductive silicone portions 102 and the body of the patient.

A simplified structure of return electrode 100 is shown in FIG. 4. It is important to have the isolation LSR (Liquid Silicone Resin) layer 104 as thin as practical, as it should be wear-proof, autoclavable, etc. Shown between the split electrode portions 102 is the capacitance Cz, i.e., the capacitance between the conductive plates, which is measured by a measurement circuit in the electrosurgical generator. The value of this capacitance changes whenever the return electrode 100 is placed on a body. Also, its value will depend on contact area, e.g., when the contact is better the capacitance will be higher.

Using the QUADTECH Precision RLC meter, measurements were made of the capacitance between the conductive plates (between the cable leads) at frequency 50 kHz. In table 1 below are the results.

TABLE 1

| | | Conditions: Fmeas = 50 kHz, 3 m cable | | | |
|---|---|---|---|---|---|
| Measured parameter | Abbr. | RE not placed on the body | 100% contact area | 50% contact area | 25% contact area |
| Capacitance | Cz | 175 pF | 1.10 nF | 750 pF | 490 pF |
| Impedance | Z | 18 kΩ | 3.1 kΩ | 4.4 kΩ | 6.5 kΩ |
| Phase angle | φ | (−)89.96° | (−)88.3° | (−)88.7° | (−)89.3° |

It could be seen that a system, measuring the capacitance, could monitor successfully the contact and, in case of insufficient contact area, stop the power and alarm the operator.

Figure 5:
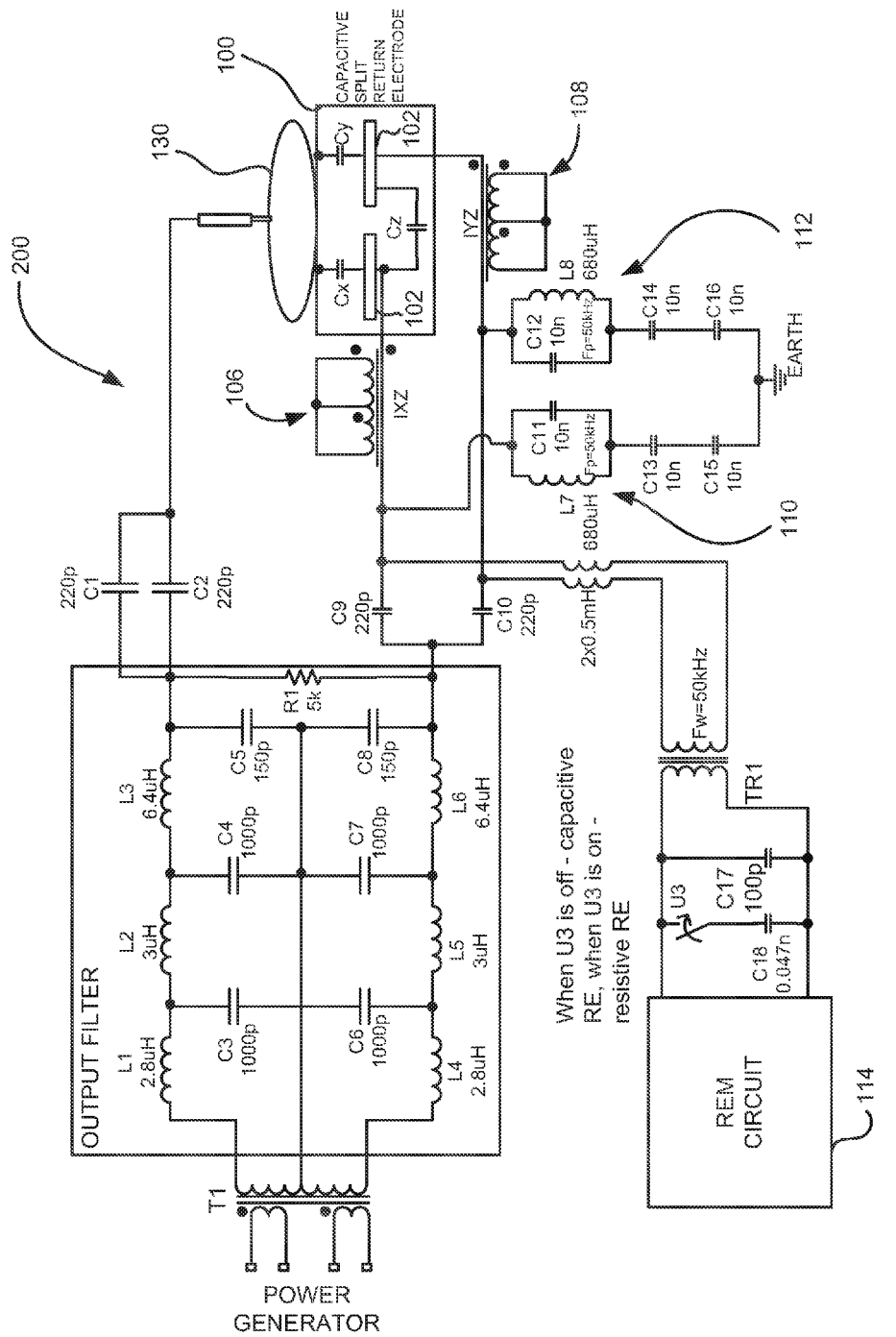
FIG. 5 is a schematic diagram of an electrosurgical return electrode monitoring system in accordance with an embodiment of the present disclosure.

Referring to FIG. 5, a schematic of a capacitively coupled return electrode (RE) monitoring system 200 in accordance with the present disclosure is provided. The system could be used also in a "resistive" mode, as will be explained in more detail below. The system includes HF (4 MHz) current monitors Ixz and Iyz, 106 and 108 respectively. The current monitors 106, 108 monitor the load current in each plate 102 of return electrode 100, and will be disposed in the housing of the electrosurgical generator (ESU). The current monitors 106, 108 are coupled to a REM (return electrode monitoring) circuit 114 which determines the capacitance between the body of the patient 130 and each conducting plate (Cx and Cy) based on the monitored current. The capacitance between the body of the patient 130 and each conducting plate (Cx and Cy), is dependent on the dielectrical properties of the LSR (Liquid Silicone Resin) film, and the contact area for each plate. In an ideal condition, the capacitance between the body of the patient 130 and each conducting plate will be equal, i.e., Cx=Cy. So a system, that can distinguish how different the capacitance Cx is from the capacitance Cy will be enough to monitor the return electrode RE 100.

The value of the capacitance, seen by the LF (low frequency 50 kHz) measurement system, will be given by:

$$Cmeas=Cz+110\ pF+(Cx*Cy/(Cx+Cy)) \rightarrow CN=Cmeas-Cz-110\ pF. \quad (1)$$

where CN is the actual return electrode (RE) capacitance in series with the load, where all other components Cz, 110 pF are excluded. For a given electrode and given schematic, the capacitance Cz is a constant one. The value 110 pF is the parallel combination between capacitors C9 and C10, which also adds to the reading. In order to prevent the reading of the earthing capacitors (C13-C16), two parallel resonance circuits 110, 112 are added for the 50 kHz measurement. Thus, for the 4 MHz working frequency, the parallel resonance circuits 110, 112 will have a very low impedance and the return electrode 100 will be connected to earth, but for the 50 kHz working frequency, the return electrode 100 will be open due to the high impedance of the parallel resonance circuits 110, 112 at 50 kHz.

If the "triangle" configuration Cx, Cy, Cz is transformed to a "star" one, and if the ratio between the currents is denoted as:

$$K=Iyz/Ixz, \quad (2)$$

and if $$CN-\text{ is the measured capacitance,} \quad (3)$$

(where Cz and all other capacitors, except Cx, Cy are subtracted), then the following equations can be derived:

$$Cx=CN(1+K)$$

$$Cy=CN(1+1/K)$$

$$K=Iyz/Ixz$$

$$Cz=\text{const} \quad (4)$$

Analyzing the system of equations (4) as shown above, the system of the present disclosure provides for the following features as will be described below.

All parameters with a HF current measurement and LF capacitive measurement can be determined enabling the system 200 to work in frequencies of 50 kHz and 4 MHz and with capacitive and resistive type return electrodes. The LF measurement can be used only in stand-by mode (avoiding noise problems), but dynamically the system 200 could monitor only by the value of K. If K is between 0.25-2.5, the capacitive contact is considered acceptable. If K is out of these boundaries, an alarm is sent to the operator.

The measurement system can be used to monitor the capacitive contact only. It can be seen from the measurements in Table 1, that the measurement system will have sufficient resolution to do that. It could be implemented by a similar rule, as in the resistive split return electrode, that is, once the capacitance is measured and is higher than the capacitance value for 30% contact area (i.e., LL-low limit), then the operator can begin the procedure. The power is delivered to the patient, unless, due to monitoring, the capacitance value is found to be below LL, or is found to be higher than 30% of the initial value.

Figure 6:
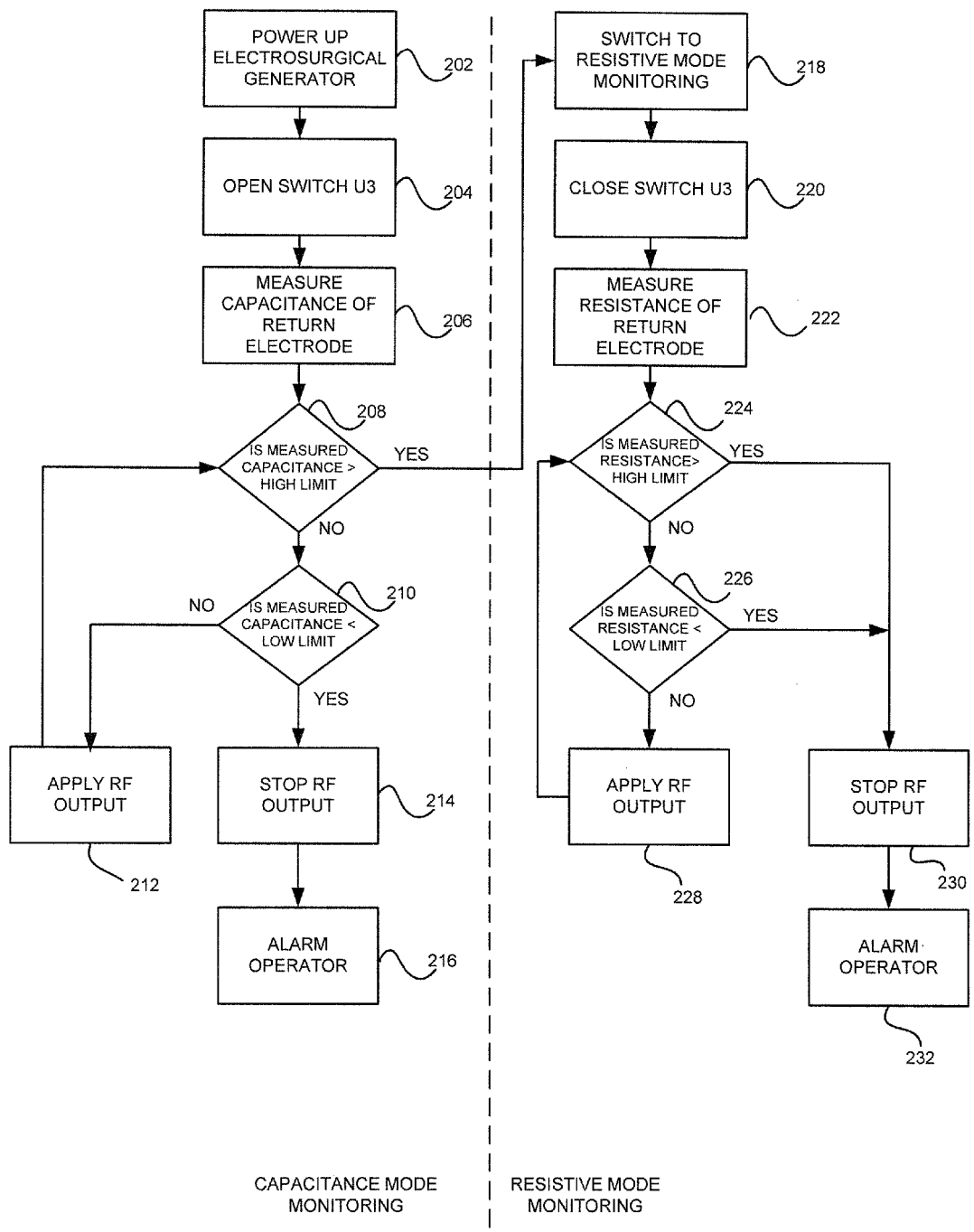
FIG. 6 is a flowchart of an exemplary method for monitoring an electrosurgical return electrode in accordance with an embodiment of the present disclosure.

The system 200 will work also with a resistive split return electrode RE. The recognition of the type of return electrode will be done automatically, as will be described in relation to FIG. 6.

Initially, in step 202, the electrosurgical generator or unit is powered up. The system is always starting with an attempt to monitor a capacitive return electrode RE, and therefore, switch U3 is placed in an open position, step 204. In step 206, the REM (return electrode monitoring) circuit 114 measures the capacitance of the return electrode 100. If the sensed capacitance is higher than the upper limit for the capacitive mode (e.g., >3 nF) in step 208, then the system will automatically switch to a resistive mode monitoring, step 218; otherwise, the system determines if the sensed capacitance is lower than a predetermined low limit, e.g., 750 pF, in step 210. If the sensed capacitance is greater than the predetermined low limit, the system determines contact is good and RF energy is applied to the tissue, step 212. If, in step 210, the sensed capacitance is less than the predetermined low limit, the system determines contact is bad and the RF energy output is stopped or not applied, step 214. Furthermore, after the RF energy output is stopped, an alarm is generated and presented to an operator, e.g., a visual or audible alarm, step 216.

If, step 208, the sensed capacitance is higher than the upper limit for the capacitive mode (e.g., >3 nF), the system automatically switches to the resistive mode monitoring, step 218. In that case, a capacitor C18 is added in the system by relay or switch U3 for noise reduction, step 220. The capacitor C18 is necessary for the normal noise-free functionality of the resistive type recognition circuit. However, in the capacitive recognition mode, the capacitor C18 will disturb the measurements being taken, and therefore is excluded from the circuit by the relay or switch U3.

The system checks to ensure the contact resistance is with the predetermined limits and then enables the application of the RF energy output. In step 222, the REM (return electrode monitoring) circuit 114 measures the contact resistance of the return electrode 100. If the contact resistance is higher than the upper limit for the resistive mode (e.g., >135 ohms) in step 224, the system will stop the RF output, step 230, and alarm the operator, step 232; otherwise, the system determines if the contact resistance is lower than a predetermined low limit, e.g., 20 ohms, in step 226. If the contact resistance is greater than the predetermined low limit, the system determines contact is good and RF energy is applied to the tissue, step 228. If, in step 226, the contact resistance is less than the predetermined low limit, the system determines contact is bad and the RF energy output is stopped or not applied, step 230. Furthermore, after the RF energy output is stopped, an alarm is generated and presented to an operator, e.g., a visual or audible alarm, step 232.

The REM (return electrode monitoring) circuit 114 will continuously monitor the return electrode 100 and issue alarms if the capacitance is outside of the acceptable limits dependent on the type of return electrode employed. After an alarm condition, the recognition process starts again—relay or switch U3 is off, check for capacitive return electrode RE. If not, relay or switch U3 is on, check for resistive return electrode RE.

Another recognition approach is leading to a more complex return electrode RE front-panel connector—each type of electrode—capacitive or resistive will have a mechanical recognition feature. Once the type of electrode is determined, the REM (return electrode monitoring) circuit 114 will place the switch U3 in the proper position and the system will monitor for alarms as described above.

It is to be appreciated that the electrode could be made also disposable. It is also contemplated by the present disclosure that a non-split resistive return electrode RE could be recognized by such a system (e.g., capacitance is over 4 uF at 50 kHz).

The described return electrode RE monitoring system will enable the 4 MHZ ESU to be equipped with an automatic recognition and monitoring system, which will give additional convenience to the operators.

While the disclosure has been shown and described with reference to certain preferred embodiments thereof, it will be understood by those skilled in the art that various changes in form and detail may be made therein without departing from the spirit and scope of the disclosure as defined by the appended claims.

Furthermore, although the foregoing text sets forth a detailed description of numerous embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

It should also be understood that, unless a term is expressly defined in this patent using the sentence "As used herein, the term '_____' is hereby defined to mean . . ." or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

What is claimed is:

1. An electrosurgical system comprising:
    an electrosurgical unit for providing electrosurgical energy at an active output thereof and for controlling the flow of the energy through the active output, the electrosurgical unit having a return input;
    an active electrode coupled to the active output for transmitting electrosurgical energy to a patient in an electrosurgical procedure;
    a return electrode adapted to be coupled to the patient for receiving electrosurgical energy supplied to the patient during the electrosurgical procedure and coupled to the return input for returning it to the return input of the electrosurgical unit;
    a measurement circuit for measuring current at the return electrode; and
    a monitoring circuit coupled to the measurement circuit for receiving the measured current and determining capacitance at the return electrode, determining a type of return electrode based on the determined capacitance and determining whether to provide the electrosurgical energy at the active output based on the type of return electrode and determined capacitance, wherein the type of return electrode is a capacitive return electrode or a resistive return electrode.

2. The electrosurgical system of claim 1, wherein if the determined capacitance is between a first predetermined value and a second predetermined value, the monitoring circuit determines the type of return electrode as a capacitive return electrode.

3. The electrosurgical system of claim 2, wherein if the determined capacitance is less than the first predetermined value, the monitoring circuit signals the electrosurgical unit to not provide the electrosurgical energy at the active output.

4. The electrosurgical system of claim 2, wherein if the determined capacitance is greater than the second predetermined value, the monitoring circuit determines the type of return electrode as a resistive return electrode.

5. The electrosurgical system of claim 4, wherein if the type of return electrode is a resistive return electrode, the monitoring circuit determines contact resistance at the return electrode based on the measured current and signals the electrosurgical unit to provide the electrosurgical energy at the active output if the determined contact resistance is between a third predetermined value and a fourth predetermined value.

6. The electrosurgical system of claim 5, wherein if the determined contact resistance is outside a range between the third and fourth predetermined values, the monitoring circuit signals the electrosurgical unit to not provide the electrosurgical energy at the active output.

7. The electrosurgical system of claim 5, wherein if the type of return electrode is a resistive return electrode, the monitoring circuit switches in noise reduction circuitry when determining the contact resistance.

8. The electrosurgical system of claim 1, wherein the return electrode is a split electrode includes a first conductive portion coupled to a second conductive portion.

9. The electrosurgical system of claim 8, wherein the first and second conductive portions are composed of silicone and are capacitively coupled by a layer of silicone resin.

10. The electrosurgical system of claim 8, wherein the measurement circuit includes a first current monitor coupled to the first conductive portion for measuring the current in the first conductive portion and a second current monitor coupled to the second conductive portion for measuring the current in the second conductive portion.

11. An electrosurgical system comprising:
an electrosurgical unit for providing electrosurgical energy at an active output thereof and for controlling the flow of the energy through the active output, the electrosurgical unit having a return input;
an active electrode coupled to the active output for transmitting electrosurgical energy to a patient in an electrosurgical procedure;
a return electrode adapted to be coupled to the patient for receiving electrosurgical energy supplied to the patient during the electrosurgical procedure and coupled to the return input for returning it to the return input of the electrosurgical unit;
a detection circuit configured to determine a type of the return electrode and to determine at least one value to monitor based on the determined type of return electrode; and
a monitoring circuit configured to monitor the at least one value of the return electrode and determining whether to provide the electrosurgical energy at the active output based on the determined type of return electrode and the monitored at least one value,
wherein the type of return electrode is a capacitive return electrode or a resistive return electrode.

12. The electrosurgical system of claim 11, wherein the detection circuit is a return electrode connector recognition device.

13. The electrosurgical system of claim 11, wherein the detection circuit monitors a capacitance of the return electrode and determines the type of return electrode based on the monitored capacitance.

14. The electrosurgical system of claim 11, wherein if the type of return electrode is a capacitive return electrode, the monitored at least one value is capacitance.

15. The electrosurgical system of claim 11, wherein if the type of return electrode is a resistive return electrode, the monitored at least one value is resistance.

16. In an electrosurgical system including an electrosurgical unit for providing electrosurgical energy at an active output, an active electrode coupled to the active output for transmitting electrosurgical energy to a patient in an electrosurgical procedure and a return electrode adapted to be coupled to the patient for receiving electrosurgical energy supplied to the patient during the electrosurgical procedure and coupled to a return input of the electrosurgical unit, a method for applying electrosurgical energy comprising:
measuring current at the return electrode;
determining capacitance at the return electrode based on the measured current;
determining a type of return electrode based on the determined capacitance; and
determining whether to provide the electrosurgical energy at the active output based on the type of return electrode and determined capacitance wherein the type of return electrode is a capacitive return electrode or a resistive return electrode.

17. The method of claim 16, wherein if the determined capacitance is between a first predetermined value and a second predetermined value, determining the type of return electrode as a capacitive return electrode.

18. The method of claim 17, wherein if the determined capacitance is less than the first predetermined value, stopping the electrosurgical energy at the active output.

19. The method of claim 17, wherein if the determined capacitance is greater than the second predetermined value, determining the type of return electrode as a resistive return electrode.

20. The method of claim 19, wherein if the type of return electrode is a resistive return electrode,
determining contact resistance at the return electrode based on the measured current and
signaling the electrosurgical unit to provide the electrosurgical energy at the active output if the determined contact resistance is between a third predetermined value and a fourth predetermined value.

21. The method of claim 20, wherein if the determined contact resistance is outside a range between the third and fourth predetermined values, signaling the electrosurgical unit to not provide the electrosurgical energy at the active output.

* * * * *